United States Patent [19]

Wheaton et al.

[11] 4,293,225
[45] Oct. 6, 1981

[54] UNDERWATER FLUOROMETER MEASURING SYSTEM

[75] Inventors: John E. G. Wheaton, London; David Griffiths, Surrey; Richard C. M. Learner, London, all of England

[73] Assignee: Chelsea Instruments Limited, London, England

[21] Appl. No.: 53,340

[22] Filed: Jun. 29, 1979

[30] Foreign Application Priority Data

Jun. 30, 1978 [GB] United Kingdom ............... 28464/78

[51] Int. Cl.³ .......................................... G01N 21/64
[52] U.S. Cl. .................. 356/417; 250/461 R
[58] Field of Search ............... 356/317, 318, 417; 250/458, 459, 461 R, 461 B

[56] References Cited

U.S. PATENT DOCUMENTS

| 3,666,945 | 5/1972 | Früngel et al. | 250/365 |
| 3,810,696 | 5/1974 | Hutchins, Jr. | 356/325 |
| 3,825,762 | 7/1974 | White | 250/458 |
| 3,832,555 | 8/1974 | Ohnishi | 250/458 |
| 3,845,309 | 10/1974 | Helm et al. | 356/317 |
| 3,975,098 | 8/1976 | West | 356/318 |
| 4,178,512 | 12/1979 | Früngel et al. | 250/461 R |
| 4,198,567 | 4/1980 | Eneroth et al. | 250/461 R |

OTHER PUBLICATIONS

Jasco FP-4, "Optional Accessories," p. 7.

Primary Examiner—Vincent P. McGraw
Attorney, Agent, or Firm—Howard L. Rose

[57] ABSTRACT

A submersible fluorometer of the type having a source transmitting light pulses into the fluid in which the fluorometer is submersed to cause material in suspension to fluoresce and a fluoroescence detector, wherein a second detector is used to measure the intensity of light output of the source during each pulse of light, the outputs of the fluorescence detector and the second detector are sampled during each pulse of light and a ratioing circuit is used to determine the intensity of the fluorescence relative to the intensity of the light causing fluorescence. This arrangement compensates the output for both short and long term drift effects particularly in the light source. Preferably both the light transmitted to the said fluid and the light received therefrom is filtered, in the first case to remove light having wavelengths equal to or longer than that of the fluorescence and in the second case to remove light having wavelengths shorter than that of the fluoroscence.

9 Claims, 6 Drawing Figures

UNDERWATER FLUOROMETER MEASURING SYSTEM

This invention relates to underwater or submersible fluorometers and methods of utilizing such instruments.

An underwater fluorometer is an instrument for measuring the fluorescence of, for example, substances in suspension or living organisms present in water, the fluorescence indicating the presence and concentration of such matter. It operates by illuminating a prescribed volume of water with light capable of producing fluorescence, and which has been filtered to remove those wavelengths which are generated by fluorescence, and then uses a detector to measure the light produced by fluorescence within that volume. So as to minimize power supply requirements, thereby enabling measurements to be taken over a prolonged period without retrieving the instrument from the water for servicing, it is normal practice to utilize a light source which generates very short but intense flashes, i.e. pulses, of fluorescent-stimulating light, such technique being essentially similar to that employed in flash photography. Difficulties arise, however due to both short term and long term drift in the characteristics of the light source. Such variations limit the inherent accuracy of the instrument and foreshorten the intervals between servicings thereof.

In the method according to the invention the said detector is enabled only for the duration of the flash of fluorescent-stimulating light, in addition the intensity of the fluorescent-stimulating light is measured directly by means of a second detector likewise only enabled during the flash, and the outputs of the two detectors are ratioed to provide a signal representative of the relative intensity of the fluorescence. By this method the measurement is made independent of the intensity and duration of the pulses of fluorescent-stimulating light and, within its operational range, ageing of the light source has no effect.

Apparatus according to the invention comprises a transmitter, a receiver, enabling means and output means, said transmitter including a pulsed light source for emitting flashes of fluorescent-stimulating light, an optical system which beams the flashes of light from said source into the fluid in which the apparatus is immersed, and a first detector which detects the light intensity of the source and provides a signal proportional thereto, said receiver including a second detector which detects the intensity of fluorescence in a specific volume of fluid illuminated by said flash of light and provides a signal proportional thereto, said enabling means enabling said source and said first and second detectors in synchronism so that the detectors are enabled only for the period during which the flash occurs, and said output means ratioing the outputs of the first and second detectors and providing an output representative of the relative intensity of the fluorescence.

Hereinafter an underwater fluorometer instrument according to the invention is further described by way of example and with reference to the accompanying drawings, wherein.

Figure 1:
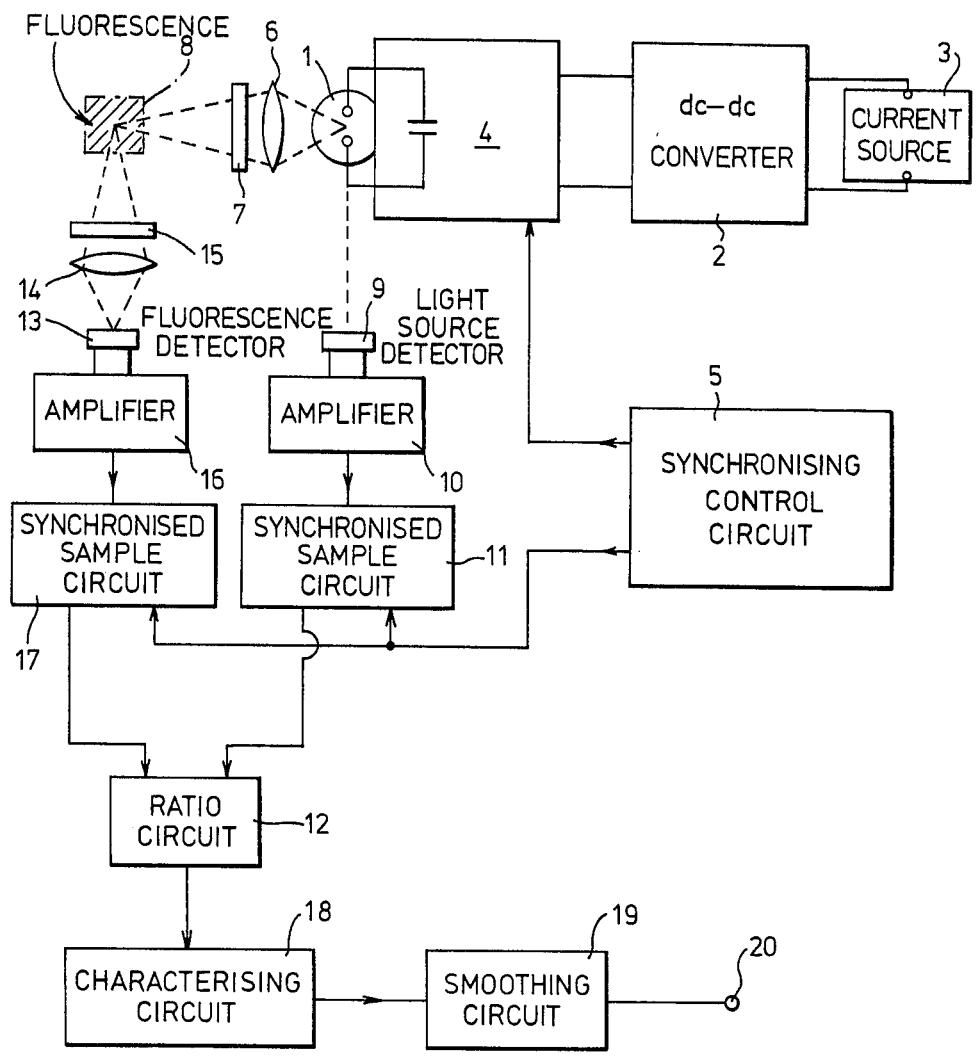
FIG. 1 shows in schematic form the functional elements of an underwater fluorometer instrument according to the invention.

Referring now to FIG. 1, a light source 1 operating from a d.c. to d.c. voltage converter 2 powered from a 24 v. supply 3 and enabled by an enabling circuit 4 generates pulses or flashes of light at intervals determined by enabling pulses supplied by control circuit 5. These pulses are usually supplied at a rate corresponding to a frequency in the range 1 to 100 Hz but the control circuit may be operated outside these limits, depending on the power available. Single pulse measurements may be made if desired. Converter 2 is of the type normally employed in photography and may be operated from a remote source or by batteries contained in the instrument.

A first optical system 6 including a filter 7 focuses the light provided by the source 1 into a predetermined space 8 occupied by the medium under test, i.e. water. Filter 7 has an optical transmission characteristic such that wavelengths comparable with and longer than those produced by fluorescence are removed from the light before it enters the said space 8. A detector 9 is disposed to receive light directly from the light source 1 and provide an input to an amplifier 10 proportional to the light intensity. A sampling circuit 11 monitors the output of amplifier 10 and provides an output signal to a first input of a ratio-determining circuit 12 during an interval determined by the control circuit 5, which interval is synchronized with the occurrence of a flash of light from the said source 1. A second detector 13 has its field of view focused into the predetermined space 8 by means of a second optical system 14 which includes a second filter 15. Filter 15 excludes from the detector any light of shorter wavelength than that produced by fluorescence.

Detector 13, which is similar to detector 9, provides an input to an amplifier 16 similar to amplifier 10. The output of amplifier 16 is connected to a second input of ratio-determining circuit 12 by means of a second sampling circuit 17 which is similar to that of circuit 11 and is enabled synchronously therewith by the control circuit 5. The output of the ratio circuit 12 is connected through a characterising circuit 18 and a smoothing circuit 19 to an output 20 of the instrument. Output 20 may be connected to a remote monitoring station by means of an underwater electrical connector. Circuit devices 4, 5, 9–12 and 16–19 all comprise standard arrangement known per se and no invention is envisaged or claimed herein in any of these devices taken individually.

The instrument operates in the following manner. Control circuit 5 produces control pulses at controllable intervals which are used to gate on the circuits 4, 11 and 17, there being suitable delays built into the controlling means of the synchronised sample circuits 11 and 17 so that they are enabled in synchronism with each other and with the occurrence of the flash provided by the light source 1. Thereby any fluorescence which occurs during the enabled period is detected by the detector 13 and a signal representative thereof is coupled by the amplifier 16 and the synchronised sample circuit 17 into the said second input of the ratio circuit 12. During the same period a signal representative of the intensity of the light flash provided by the light source 1, as detected by detector 9, is coupled into the first input of the ratio circuit 12 by means of amplifier 10 and synchronised sample circuit 11. The ratio of these signals is determined in the said circuit 12 and output therefrom is fed through characterising circuit 18 and smoothing circuit 19 to the output 20. The time constant of the smoothing circuit 19 and the frequency of the enabling pulses provided by the control circuit 5 are normally chosen so that under normal operation the output from the ratio-determining circuit is a continuous one. The characterising circuit 18 will usually have a logarithmic transfer characteristic, but a linear characteristic may be preferred for some applications.

Since the level of intensity of fluorescence is normally directly proportional to the intensity of the stimulating light, it follows that any variation in the latter will cause a proportional change in the level of fluorescence detected. These variations therefore cancel in the ratio circuit 12 with the consequence that the instrument is insensitive to the absolute level of intensity of fluorescence. For the same reason the instrument is also insensitive to ageing effects in the light source 1 and variations in the voltage of the power supply 3 or the performance of the converter 2.

Figure 2:
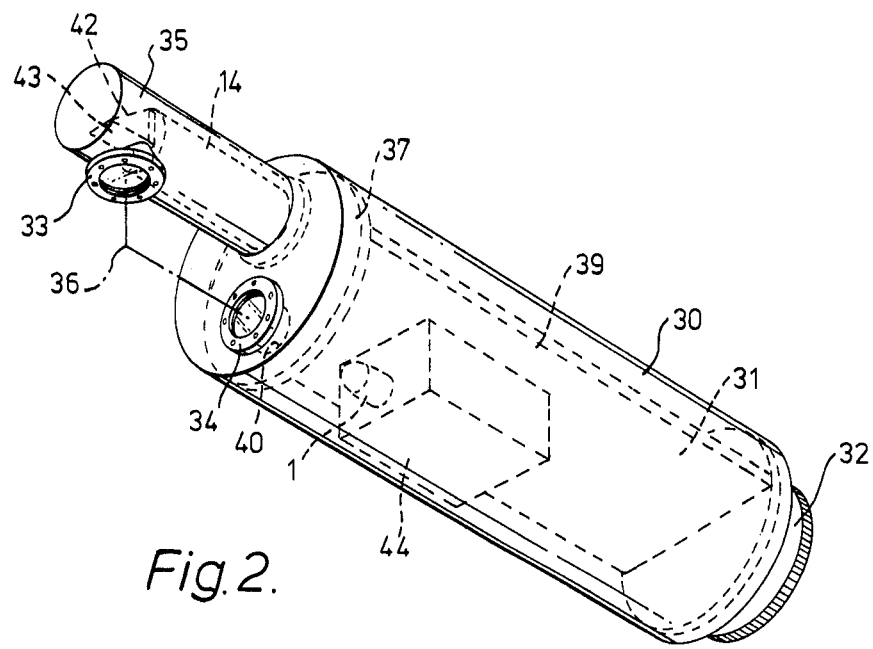
FIGS. 2 and 3 show, respectively, the external and internal construction of a preferred form of the fluorometer instrument indicated schematically in FIG. 1.
Figure 3:
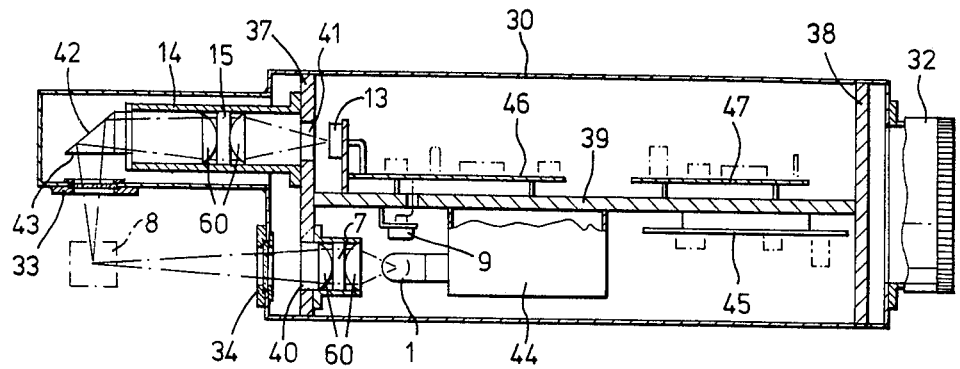

Referring now to FIGS. 2 and 3, there is shown the external case 30 which houses the optical systems and circuit devices illustrated in FIG. 1 and, in ghosted outline, an internal, removable, bobbin 31 on which the said devices are mounted.

The case 30 takes the form of a water-tight pressure-resisting container having an underwater electrical connector 32 at one end and first 33 and second 34 windows at the end of the case remote from the electrical connector. Window 33 is formed in the side wall of a fixed cylindrical turret 35 formed on the axial end face of the case 30 whilst window 34 is formed in the said axial end face of the case. The optical axes of these windows lie in a common plane and meet at a point 36 external to the case, within the aforesaid space 8.

Various materials are suitable for constructing the case 30, one of the most suitable being aluminium because of the ease with which it can be formed into an hermetic enclosure, and because it is an inherently cheap material. Aluminium, however, is readily corroded and where prolonged exposure to polluted environments is expected, particularly if the instrument is to be immersed in salt water for long periods, a titanium alloy case may be preferred. Titanium alloy cases are also particularly suited where the instrument is likely to be towed behind a vessel in salt water because it has been found that the life of an aluminium case is considerably foreshortened where there is fairly high relative movement between the case and a salt water medium in which it is immersed. For its added strength, a stainless steel case may be preferred in deep water applications.

Figure 4:
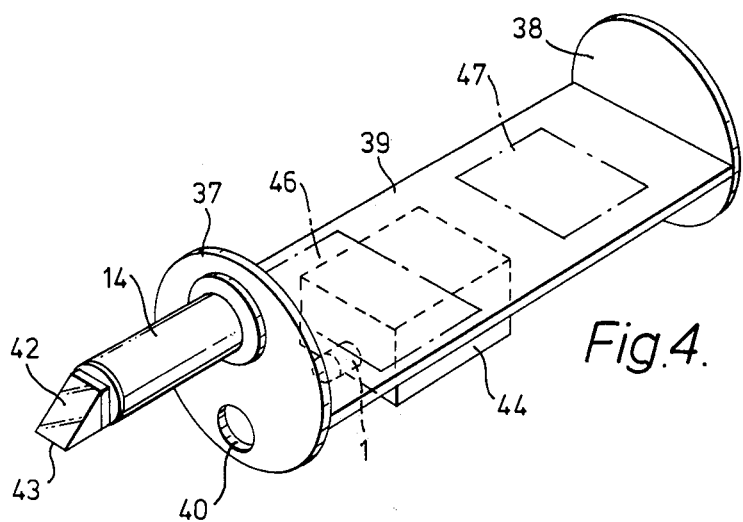
FIG. 4 shows the removable bobbin on which the various internal parts of the fluorometer are mounted.

As best seen in FIG. 4, the bobbin 31, which would normally be constructed of aluminium or similar material having good structural and electrical-screening properties, comprises a pair of flanges 37, 38, each having a diameter such as to allow the bobbin to fit snugly within the case 30, mounted parallel to one another at each end of a metal plate 39 of a width substantially equal to the diameter of the flanges.

Flange 37 mounts the said optical systems 6 and 14 which are fixed thereon in alignment respectively with apertures 40 and 41. These apertures are also aligned respectively with the window 34 and the turret 35 and allow passage of the light from the light source 1 to the window 34 on the one hand, and through the optical system 14 to the detector 30 on the other hand. Flange 38 acts mainly as an alignment means but plate 39 is used both to screen the optical radiation associated with system 6 from that associated with system 14 and for mounting the electrical devices and the electronic components of the said circuit devices. Plate 39 serves also as an electrical screen.

Figure 6:
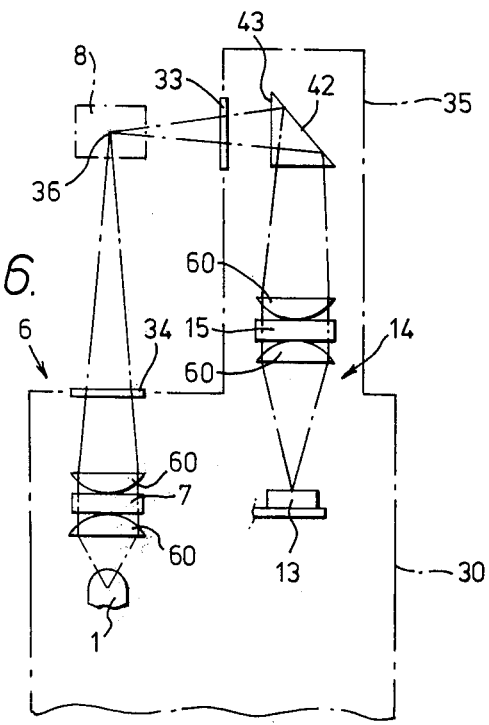
FIG. 6 shows in larger scale the arrangement of optics in FIG. 3.

As best seen in FIGS. 3 and 6, optical system 14 comprises a lens arrangement, in a mount, which registers with the turret 35 and images the light emitted in space 8 onto the light-sensitive face of detector 13. The latter is mounted from the plate 39 by means of a bracket in alignment with and immediately behind the aperture 41. System 14 includes a prism 42 mounted on an end window placed at the end of the mount remote from the flange 37, for example by means of a suitable adhesive. The orthogonal face 43 of the prism 42 is positioned so as to align with the window 33. Light source 1 which may comprise, for example, a xenon flash tube, or other suitable emitter of ultra-violet light, is mounted directly upon a housing 44 which itself is mounted upon the underside of plate 39 (as seen in FIG. 3). Housing 44 contains the converter 2. The components for the synchronizing control circuit 5 and the enabling circuit 4 are all contained on a printed circuit board 45 likewise mounted on the underside of the plate 39. Amplifiers 10 and 16, synchronized sample circuits 11 and 17, ratio circuit 12, characterising circuit 18 and smoothing circuit 19 are all mounted on one or other of the printed circuit boards 46, 47, shown mounted on the top side of plate 39. Detector 9 is mounted by means of a bracket on the underside of the plate 39 in close proximity to the light source 1 such that it is illuminated thereby.

Figure 5:
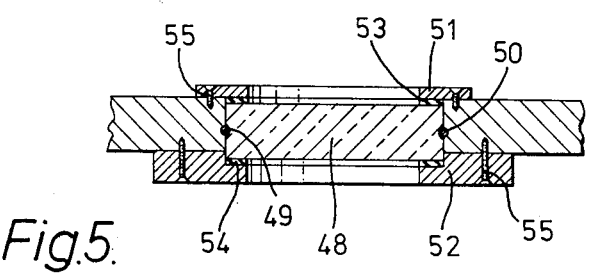
FIG. 5 is a detailed drawing showing the preferred method of hermetically mounting the windows in the external case.

Referring now to FIG. 5, each window comprises a thick disc 48 of material having suitable optical properties, e.g. perspex, glass, quartz, etc., which is circumferentially recessed with a groove 49 at the medial plane to receive an O-ring 50. Annular flanges 51, 52 retain the disc in the respective aperture in the end face or the turret, there being suitable annular gaskets 53, 54 inserted between the disc and the retaining flanges 51, 52. Annular flanges 51 and 52 are fixed in position on the end face or the turret by suitable attachment means such as screws 55.

FIG. 6 shows in greater detail the two optical systems 6 and 14 and their physical relationship. Each system basically comprises a pair of plano-convex lenses 60 between which is placed the appropriate filter 7 and 15. The lens and windows are formed of appropriate materials relative to the wavelengths of the light to be transmitted thereby, i.e. perspex, glass, quartz, etc.

System 6 transmits light from the light source 1 through the window 34 and focuses it at point 38 in space 8. Optical system 14 receives the light emitted in space 8 which passes through the window 33 and falls upon prism 42 and condenses this light onto the light-sensitive surface of detector 13. The outline of the associated parts of case 1 and the turret 35 are shown in ghosted outline in FIG. 6.

In use the instrument may be deposited at some fixed point in an estuary or a river, etc. and in these circumstances it would usually be strapped directly to some permanent structural member. It may also be towed directly behind a vessel or, more usually, mounted in a fish which is itself towed behind the vessel. In these circumstances, of course, arrangements would be made to admit the water under test into the space 8 in the vicinity of the case 1.

A cable connection to a remote monitoring station may be taken from the underwater connector 32 but in an alternative form, not shown herein, electrical recording means may be incorporated within the device which may also contain suitable storage batteries or power sources to enable a prolonged immersion in the medium under test without need for intermediate servicing.

Dimensionally the instrument shown has a length of about 24 inches and a diameter of 4½ inches. Its buoyancy is such that it almost floats, but of course it can be made heavier for deep water applications.

While there have been disclosed specific methods and apparatus exemplary of the principles of the invention, it is to be understood that these are preferred forms of the invention, and that the invention may be constructed and practiced in a variety of shapes, sizes, modifications and methods without departing from the spirit and scope thereof. Accordingly, the invention is not to be limited by the specific structures and methods disclosed, but only by the subjoined claims.

We claim:

1. A submersible fluorometer instrument comprising a fluid-tight pressure case containing a light transmitter adjacent to a first window in an exterior wall of the case and a light receiver adjacent to a second window in an exterior wall of the case, said windows arranged substantially orthogonally and having axes which intersect externally of said case and in a common plane, said light transmitter comprising a controllable pulsed light source for emitting flashes of fluorescent stimulating light, a first optical system which beams the flashes of light from said source through said first window into the fluid in which the instrument is immersed and a first light detecting means arranged to detect the intensity of light emitted by the said pulsed light source, and said light receiver comprising a second optical system arranged coaxially with said second window to receive light emissions from a specific volume of the fluid illuminated by said flash of light and to transmit said light emissions to a second detector, wherein said first optical system incorporates a filter which removes from the light transmitted through the first said system any light having a wavelength equal to or longer than that produced by the fluorescence and the second optical system incorporates a filter which removes from the light transmitted through the second said system any light having a wavelength shorter than that produced by the fluorescence, said fluid-tight pressure case further containing a synchronising control means for enabling the flashes of light, a first synchronised sampling means coupled to the said control means so as to be enabled thereby in synchronism with the said flashes of light, said first synchronised sampling means being connected to sample the output of the first detecting means, a second synchronised sampling means coupled to the control means so as to be enabled thereby in synchronism with the said flashes of light and the said first synchronised sampling means, said second synchronised sampling means being connected to sample the output of the second detecting means, ratioing means coupled to said first and second sampling means for determining a ratio of the synchronised samples of the said first and second sampling means, said ratioing means providing an output signal proportional to the value of the said ratio, and output means for providing a signal representative of the fluorescence detected by the second detector relative to the energy in the respective flashes of light transmitted into the said fluid.

2. The submersible fluorometer instrument of claim 1 wherein the output means comprises signal characterising means and signal smoothing means.

3. The submersible fluorometer instrument of claim 2 wherein the characterising means has a logarithmic transfer characteristic.

4. The submersible fluorometer instrument of claim 2 wherein the characterising means has a linear transfer characteristic.

5. A submersible fluorometer instrument comprising a fluid-tight pressure case containing a light transmitter adjacent to a first window in an exterior wall of the case and a light receiver adjacent to a second window in an exterior wall of the case, said windows arranged substantially orthogonally and having axes which intersect externally of said case and in a common plane, said light transmitter comprising a controllable pulsed light source for emitting flashes of fluorescent stimulating light, a first optical system which beams the flashes of light from said source through said first window into the fluid in which the instrument is immersed and a first light detecting means arranged to detect the intensity of light emitted by the said pulsed light source, and said light receiver comprising a second optical system arranged coaxially with said second window to receive light emissions from a specific volume of the fluid illuminated by said flash of light and to transmit said light emissions to a second detector, wherein said first optical system incorporates a filter which removes from the light transmitted through the first said system any light having a wavelength equal to or longer than that produced by the fluorescence and the second optical system incorporates a filter which removes from the light transmitted through the second said system any light having a wavelength shorter than that produced by the fluorescence, said fluid-tight pressure case further containing a synchronizing control means for enabling the flashes of light, a first synchronized sampling means coupled to the said control means so as to be enabled thereby in synchronism with the said flashes of light, said first synchronized sampling means being connected to sample the output of the first detecting means, a second synchronized sampling means coupled to the control means so as to be enabled thereby in synchronism with the said flashes of light and the said first synchronized sampling means, said second synchronized sampling means being connected to sample the output of the second detecting means, and means for providing a signal representative of the fluorescence detected by the second detector.

6. In a submersible fluorometer, the improvement comprising, in combination,
a unitary housing having external walls which form a fluid-tight case and an internal wall dividing said housing into first and second chambers which are optically and electrically isolated from each other,
a first window in a said external wall for optically coupling a first prescribed volume of fluid external of the housing with said first chamber, a second window in a said external wall for optically coupling a second prescribed volume of fluid with the said second chamber, said first and second windows having substantially orthogonal optical axes which intersect at a point within said prescribed volumes whereby to define a measured volume of fluid, a light transmitter arranged in said first chamber comprising a controllable impulsively driven light source for emitting flashes of fluorescent stimulating light over a wide band of wavelengths at controllable instances in time, a first optical system in said first chamber which beams said flashes of light through said first window into said first prescribed volume, said first optical system having filter means for removing from said beam any light having wavelengths equal to or longer than that produced by fluorescence within the measured volume of fluid, a first light detecting means in said first chamber arranged to detect the intensity of light emitted by the said light source and provide an output corresponding thereto, a fluorescent light receiver in said second chamber comprising a second light detecting means arranged to receive light emissions from said measured volume of fluid through a second optical system and through said second window along a path coaxial with the optical axis of the said window, said second optical system having filter means for removing from the received emissions any light having wavelengths shorter than that produced by the said fluorescence, said light source and said second light detecting means being arranged to respectively transmit and receive light along parallel axes and one of said first and second optical systems having means for turning the path of said light through 90 degrees, said housing further containing light source energizing means, first and second sampling means for respectively sampling said first and second detecting means, synchronizing control means for enabling said light source energizing means and said first and second sampling means in synchronism at predetermined intervals, said first and second sampling means being energized for the duration of the light pulses, ratioing means coupled to said first and second sampling means, and output means for providing a signal representative of the fluorescence detected by said second detector relative to the energy in the respective flashes of light transmitted into the said fluid.

7. The submersible fluorometer of claim 6 wherein the output means comprises signal characterizing means and signal smoothing means.

8. The submersible fluorometer of claim 7 wherein the characterizing means has a logarithmic transfer characteristic.

9. The submersible fluorometer of claim 8 wherein the characterizing means has a linear transfer characteristic.

* * * * *